United States Patent [19]

Fancher

[11] 4,356,022
[45] Oct. 26, 1982

[54] S-ALKYL AND ALKENYL-THIOPHENYLACETAMIDO THIOPHOSPHATES AND PHOSPHONATES AS PLANT GROWTH REGULANTS

[75] Inventor: Llewellyn W. Fancher, New Castle, Calif.

[73] Assignee: Stauffer Chemical Company, Westport, Conn.

[21] Appl. No.: 227,018

[22] Filed: Jan. 21, 1981

Related U.S. Application Data

[62] Division of Ser. No. 133,066, Mar. 24, 1980, Pat. No. 4,283,395.

[51] Int. Cl.³ ............... A01N 57/14; C07F 9/165; C07F 9/40
[52] U.S. Cl. ........................................ 71/87; 260/943
[58] Field of Search ............................................. 71/87

[56] References Cited
U.S. PATENT DOCUMENTS 3,013,940 12/1961 Fusco et al. .................. 260/943
3,057,774 10/1962 Baker et al. .................. 260/943
3,106,510 10/1963 Szabo et al. .................. 260/943
4,016,266 4/1977 Gutman ........................ 260/943
4,152,428 5/1979 Salbeck et al. ............... 260/943
4,278,461 7/1981 Salbeck et al. ............... 71/87

FOREIGN PATENT DOCUMENTS 1016666 1/1966 United Kingdom ............... 260/943

Primary Examiner—Anton H. Sutto
Attorney, Agent, or Firm—Joel G. Ackerman

[57] ABSTRACT

Novel compounds having the formula

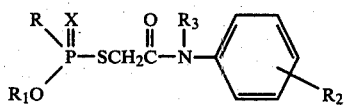

in which R is lower alkyl, $R_2$ is thio-lower alkyl or thio-lower alkenyl, $R_3$ is hydrogen or lower alkyl and X is oxygen or sulfur, provided that when X is oxygen, R is lower alkoxy, have shown utility as insecticides and miticides and in some cases as plant growth regulators.

2 Claims, No Drawings

S-ALKYL AND ALKENYL-THIOPHENYLACETAMIDO THIOPHOSPHATES AND PHOSPHONATES AS PLANT GROWTH REGULANTS

This is a division of application Ser. No. 133,066, filed Mar. 24, 1980, now U.S. Pat. No. 4,283,395.

BACKGROUND OF THE INVENTION

This invention relates to novel compounds having the formula

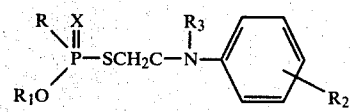

in which R is lower alkyl or lower alkoxy; $R_1$ is lower alkyl; $R_2$ is thio-lower alkyl or thio-lower alkenyl; $R_3$ is hydrogen or lower alkyl and X is oxygen or sulfur; provided that when X is oxygen, R is lower alkoxy.

By the terms "lower alkyl" and "lower alkoxy" are meant such groupings having from 1 to 6 carbon atoms. Examples of lower alkyl groups are methoxy, ethoxy, isopropoxy, and isobutoxy. Examples of lower alkyl groups are methyl, ethyl, n-propyl, isopropyl, n-butyl, and n-amyl. Preferably, the lower alkyl and lower alkoxy groups have from 1 to 4 carbon atoms. The term "lower alkenyl" includes such groupings having from 2 to 5 carbon atoms and at least one double bond. A preferred member of this group is allyl. The terms "thio-lower alkyl" and "thio-lower alkenyl" include groupings as defined under "lower alkyl" and "lower alkenyl" additionally including a sulfur atom. The thio-lower alkyl or thio-lower alkenyl group may be substituted on the phenyl ring at the ortho, meta or para position. In general, the para-substituted compounds show the highest activity.

In one embodiment of this invention, X is sulfur and R is lower alkyl; these compounds are dithiophosphonates. In another embodiment, X is sulfur and R is lower alkoxy; such compounds are dithiophosphates. In a third embodiment, X is oxygen and R is lower alkoxy, making such compounds monothiophosphates.

In another aspect, this invention relates to a method of controlling or combatting insects or mites by applying an insecticidally or miticidally effective amount of a compound as defined herein to the insect or the habitat thereof, or to a locus at which insecticidal or miticidal protection is desired.

In still another aspect, this invention relates to insecticidal or miticidal compositions of matter comprising an insecticidally or miticidally effective amount of a compound as defined herein with an insecticidally or miticidally suitable diluent or carrier.

In addition, certain of the compounds of this invention have also been found to possess plant growth regulatory activity; several compounds have also been found to be fungicides.

In general the compounds of the invention may be prepared by a three-step process.

In the first step, an aminothiophenol is reacted with a lower alkyl or lower alkenyl halide in the presence of an acid acceptor (such as triethylamine) and a solvent (such as benzene or tetrahydrofuran) to produce an amino (alkyl or alkenyl) thiophenol:

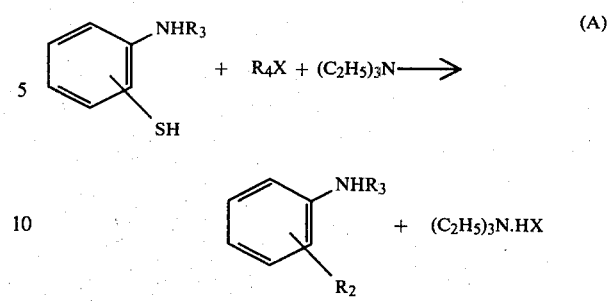

in which $R_4$ is lower alkyl or alkenyl, X is a halogen and $R_2$ and $R_3$ are as defined above.

In the second step, the product of step (a) is reacted with chloroacetic anhydride or chloroacetyl chloride in the presence of a solvent (such as tetrahydrofuran) and a base, preferably N,N-dimethylaniline, to produce a chloroacetamide-substituted thiophenol:

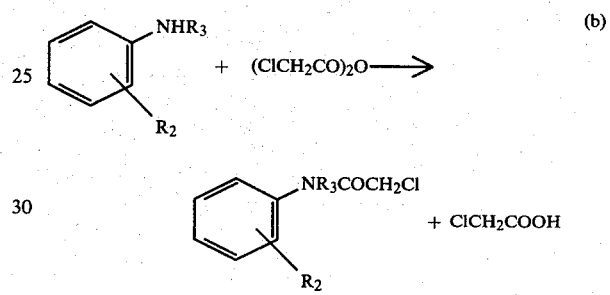

This product is then reacted with a thiophosphate or thiophosphonate (as the acid or an alkali metal salt) to produce the desired product:

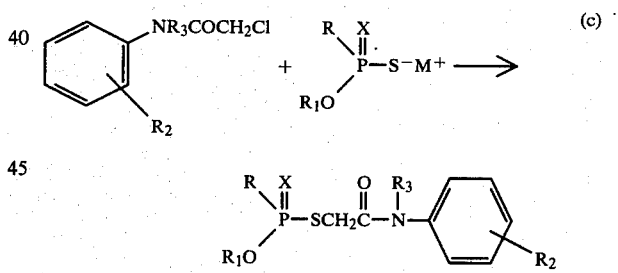

in which M is an alkali metal or hydrogen and R and $R_1$ are as previously defined.

Reaction (c) is conducted in the presence of a base (such as triethylamine) and a solvent (such as tetrahydrofuran). All reactions are conducted at atmospheric pressure. Temperatures are in the range of 25°–100° C. [reaction (a)], −25° to 70° C. [reaction (b)], and 20°–40° C. [reaction (c)].

Preparation of compounds of this invention by such method is illustrated in the following examples.

EXAMPLE 1

Preparation of intermediate compounds

This example illustrates the preparation of an intermediate, in particular o-S-ethylmercapto chloroacetanilide, by reactions (a) and (b). Other chloroacetamides utilized in subsequent examples may be similarly prepared using analogous materials.

(a) Twenty-five grams (g) (0.2 moles) (m) o-aminothiophenol was dissolved in 50 milliliters (ml) benzene. The mixture was stirred while 20.2 g. (0.2 m.) triethylamine was rapidly added. The temperature rose to 45° C.; a solid formed. The mixture was cooled to 40° C. and 34.3 g. (0.22 m) ethyl iodide was added portionwise, with cooling to below 60° C. The mixture was then stirred and refluxed for one hour, then cooled to 25° C. Additional benzene was added and the mixture was washed with three 150 ml. portions of water, dried over MgSO4, filtered, vacuum evaporated and air-stripped on a steam bath for a short time. A yellow product was obtained (24.9 g., 81% of theoretical yield), $n_D^{30}$ 1.5955, identified as o-aminophenyl-S-ethyl sulfide. The structure was confirmed by nuclear magnetic resonance (nmr) spectroscopy.

(b) There were mixed 15.3 g. (0.1 m) o-aminophenyl-S-ethyl sulfide, 12.1 g. (0.1 m) N,N-dimethylaniline and 30 ml. tetrahydrofuran. The mixture was cooled to 15° C.; then 22.2 g. (0.13 m) chloroacetic anhydride was added portionwise with cooling to below 25° C. The mixture was warmed on a steam bath for 5 minutes, then cooled and poured into 100 ml. water. Concentrated hydrochloric acid (25 ml.) was added; the mixture was thoroughly stirred, then extracted with 100 ml. benzene. The benzene solution was washed twice with 250 ml. portions of dilute aqueous sodium chloride, dried over anhydrous MgSO4, filtered, vacuum evaporated and air stripped on a steam bath for 10 minutes. There was obtained 21.6 g. (93.9% of theoretical yield) of o-S-ethylmercapto chloroacetanilide, a brown liquid, $n_D^{30}$ 1.5752. The structure was confirmed by nmr.

EXAMPLE 2

Preparation of o-S-ethylmercapto-O,O-diethyl phosphorodithioylacetanilide (Compound 5 herein)

To a flask containing 25 ml. tetrahydrofuran there was added 2.73 g. (0.01 ml.) potassium O,O-diethyldithiophosphate. There was then added 2.30 g. (0.01 m) o-S-ethylmercapto chloroacetanilide. The mixture was stirred for 4 hours. The solvent was evaporated off and the residue dissolved in benzene, washed 3 times with 100 ml. portions of dilute aqueous sodium chloride, dried over MgSO4, filtered and evaporated. There was obtained 3.39 g. (89% of theoretical yield) of the desired product, $n_D^{30}$ 1.5755. The structure was confirmed by nmr and IR (infrared) spectroscopy.

EXAMPLE 3

Preparation of o-S-allylmercapto-O,O-diethylphosphorodithioylacetanilide (Compound 16 herein)

Similarly to Example 2, from 2.73 g. (0.012 m) potassium O,O-diethyldithiophosphate and 2.42 g. (0.01 m) o-S-allylmercapto chloroacetanilide there was obtained 3.56 g. (91% of theoretical yield), $n_D^{30}$ 1.5800. The structure was confirmed by nmr and IR spectroscopy.

EXAMPLE 4

Preparation of o-S-ethylmercapto-ethyl-O-ethylphosphonodithioylacetanilide (Compound 6 herein)

Similarly to Example 2, from 3.40 g. (0.02 m) ethyl, O-ethylphosphonodithioic acid, 3.44 g. (0.015 m) o-S-ethylmercaptochloroacetanilide and 2.01 g. (0.02 m) triethylamine, there was obtained 5.12 g. (94% of theoretical yield) of the desired product, $n_D^{30}$ 1.5880. The structure was confirmed by nmr and IR spectroscopy.

EXAMPLE 5

Preparation of o-S-ethylmercapto-N-ethyl,ethyl,O-isopropylphosphonodithioyl acetanilide (Compound 31 herein)

To a flask containing 40 ml. tetrahydrofuran there was added 3.86 (0.015 m) o-S-ethylmercapto-N-ethyl chloroacetanilide and ethyl O-isopropyl phosphorodithioic acid. The mixture was cooled to 10° C. and 1.72 g. (0.017 m) triethylamine was added. The pH was adjusted to 7 and the mixture was stirred at ambient temperature for 4 hours. The product was recovered as in Example 2. There was obtained 4.88 g. (81% of theoretical yield) of the desired product, $n_D^{30}$ 1.5724. The structure was confirmed by nmr and IR spectroscopy.

The following Table 1 contains representative compounds of this invention.

TABLE I

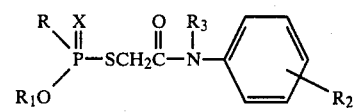

| Compound No. | R | $R_1$ | $R_2$ | $R_3$ | X | m.p., °C. or $n_D^{30}$ |
|---|---|---|---|---|---|---|
| 1 | $C_2H_5O$ | $C_2H_5$ | o-$SCH_3$ | H | S | 1.5774 |
| 2 | $C_2H_5$ | $C_2H_5$ | o-$SCH_3$ | H | S | 1.5950 |
| 3 | $C_2H_5$ | i-$C_3H_7$ | o-$SCH_3$ | H | S | 1.5876 |
| 4 | $CH_3O$ | $CH_3$ | o-$SCH_3$ | H | S | 1.5893 |
| 5 | $C_2H_5O$ | $C_2H_5$ | o-$SC_2H_5$ | H | S | 1.5755 |
| 6 | $C_2H_5$ | $C_2H_5$ | o-$SC_2H_5$ | H | S | 1.5880 |
| 7 | $CH_3O$ | $CH_3$ | o-$SC_2H_5$ | H | S | 1.5810 |
| 8 | $C_2H_5O$ | $C_2H_5$ | o-S—n$C_3H_7$ | H | S | 1.5720 |
| 9 | $CH_3O$ | $CH_3$ | o-S—n$C_3H_7$ | H | S | 1.5736 |
| 10 | $C_2H_5$ | $C_2H_5$ | o-S—n-$C_3H_7$ | H | S | 1.5858 |
| 11 | $C_2H_5$ | $C_2H_5$ | o-$SCH_3$ | $CH_3$ | S | 1.5984 |
| 12 | $C_2H_5O$ | $C_2H_5$ | o-$SCH_3$ | $CH_3$ | S | 95-99 |
| 13 | $C_2H_5O$ | $C_2H_5$ | o-S—i-$C_3H_7$ | H | S | 1.5688 |
| 14 | $CH_3O$ | $CH_3$ | o-S—i-$C_3H_7$ | H | S | 1.5785 |
| 15 | $C_2H_5$ | $C_2H_5$ | o-S—i-$C_3H_7$ | H | S | 1.5837 |
| 16 | $C_2H_5O$ | $C_2H_5$ | o-$SCH_2CH=CH_2$ | H | S | 1.5800 |
| 17 | $C_2H_5$ | $C_2H_5$ | o-$SCH_2CH=CH_2$ | H | S | 1.5936 |
| 18 | $CH_3O$ | $CH_3$ | o-$SCH_2CH=CH_2$ | H | S | 1.5896 |
| 19 | $C_2H_5O$ | $C_2H_5$ | p-$SC_2H_5$ | H | S | 1.5887 |
| 20 | $C_2H_5$ | $C_2H_5$ | p-$SC_2H_5$ | H | S | 1.6032 |
| 21 | $CH_3O$ | $CH_3$ | p-$SC_2H_5$ | H | S | 1.6011 |
| 22 | $C_2H_5$ | i-$C_3H_7$ | p-$SC_2H_5$ | H | S | 1.5939 |
| 23 | $C_2H_5O$ | $C_2H_5$ | m-$SC_2H_5$ | H | S | 1.5862 |
| 24 | $C_2H_5$ | $C_2H_5$ | m-$SC_2H_5$ | H | S | 1.5966 |
| 25 | $CH_3O$ | $CH_3$ | m-$SC_2H_5$ | H | S | 1.5992 |
| 26 | $C_2H_5$ | i-$C_3H_7$ | m-$SC_2H_5$ | H | S | 1.5884 |
| 27 | $C_2H_5$ | i-$C_4H_9$ | p-$SC_2H_5$ | H | S | 1.5884 |
| 28 | $C_2H_5$ | i-$C_4H_9$ | m-$SC_2H_5$ | H | S | 1.5798 |
| 29 | $C_2H_5$ | $C_2H_5$ | o-$SC_2H_5$ | $C_2H_5$ | S | 1.5770 |
| 30 | $C_2H_5O$ | $C_2H_5$ | o-$SC_2H_5$ | $C_2H_5$ | S | 1.5665 |
| 31 | $C_2H_5$ | i-$C_3H_7$ | o-$SC_2H_5$ | $C_2H_5$ | S | 1.5724 |
| 32 | $C_2H_5$ | $C_2H_5$ | o-S—n-$C_3H_7$ | n-$C_2H_7$ | S | 1.5800 |
| 33 | $C_2H_5O$ | $C_2H_5$ | o-S—n-$C_3H_7$ | n-$C_3H_7$ | S | 1.5663 |
| 34 | $C_2H_5$ | $C_2H_5$ | o-S—n-$C_4H_9$ | n-$C_4H_9$ | S | 1.5633 |
| 35 | $C_2H_5O$ | $C_2H_5$ | o-S—n-$C_4H_9$ | n-$C_4H_9$ | S | 1.5496 |
| 36 | $C_2H_5$ | $C_2H_5$ | p-S—n-$C_4H_9$ | H | S | 1.5923 |
| 37 | $C_2H_5O$ | $C_2H_5$ | p-S—n-$C_4H_9$ | H | S | 1.5816 |
| 38 | $C_2H_5$ | $CH_3$ | p-S—n-$C_4H_9$ | H | S | 1.6051 |
| 39 | $CH_3O$ | $CH_3$ | p-S—n-$C_4H_9$ | H | S | 1.5960 |
| 40 | $C_2H_5$ | $C_2H_5$ | p-S—n-$C_5H_{11}$ | n-$C_5H_{11}$ | S | 1.5431 |
| 41 | $C_2H_5O$ | $C_2H_5$ | o-S—$C_2H_5$ | H | O | 1.5608 |

The structure of these compounds were confirmed by infrared (ir) and/or nuclear magnetic resonance (nmr) spectral analyses.

INSECTICIDAL EVALUATION

The compounds in the above Table 1 were tested for insecticidal activity against the following insects:

Housefly [*Musca domestica* (Linn.)]
German Roach [*Blatella germanica* (Linn.)]
Lygus Bug [*Lygus hesperus* (Knight)]
Black Bean Aphid [*Aphis fabae* (Scop.)]
Green Peach Aphid [*Myzus persicae* (Sulzer)]
Saltmarsh Caterpillar [*Estigmene acrea* (Drury)]
Tobacco Budworm [*Heliothis virescens* (Fabricius)]
Cabbage Looper [*Trichoplusia ni* (Hübner)]
Southern House Mosquito [*Culex pipiens quinquefasciatus* (Say)]

The following testing procedures were used for this evaluation.

Housefly [*Musca domestica*]

Test compounds were diluted in acetone and aliquots pipetted onto the bottom of 55×15 mm aluminum dishes. To insure even spreading of the chemical on the bottom of the dishes, 1 milliliter of acetone containing 0.02% peanut oil was also added to each dish. After all solvents had evaporated, the dishes were placed in circular cardboard cages containing 25 female houseflies, one to two days old. The cages were covered on the bottom with cellophane and on the top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD-50 values are expressed below in Table II under the heading "HF", in terms of μg of the test compound per 25 female flies.

German Cockroach [*Blatella germanica* (Linn.)]

Test compounds were diluted in a 50—50 acetone-water solution. 2 cc of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% down to that at which approximately 50% mortality occurred. LD-50 values are expressed below in Table II under the heading "GR" in terms of percent of the test compound in the sprayed solution.

Lygus Bug [*Lygus hesperus* (Knight)]

Test compounds were diluted in a 50—50 acetone-water solution. 2 cc of the solution was sprayed through a hand spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid [*Aphis fabae* (Scop.)]

Nasturtium plants (*Tropaeolum* sp.) approximately 5 cm tall, were transplanted into sandy loam soil in 3-inch clay pots and infested with 25–50 black bean aphids of mixed ages. 24 hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "BA" in terms of percent of the test compound in the sprayed solution.

Green Peach Aphid [*Myzus persicae* (Sulzer)]

Radish plants (*Rhaphanus sativus*), approximately 2 cm tall, were transplanted into sandy loam soil in 3-inch clay pots and infested with 25-50 green peach aphids of mixed ages. 24 hours later they were sprayed to the point of runoff with 50—50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "GPA" in terms of percent of the test compound in the sprayed solution.

Saltmarsh Caterpillar (*Estigmene acrea* (Drury))

Test compounds were diluted in a 50—50 acetone-water solution. Sections of curly dock (*Rumex crispus*) leaves, approximately 1×1.5 inches, were immersed in the test solution for 2-3 seconds and placed on a wire screen to dry. The dried leaves were placed in petri dishes containing a moistened piece of filter paper and infested with 5 second-instar saltmarsh larvae. Mortality of the larvae was recorded 48 hours later, and a piece of synthetic media was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC" in terms of percent of the test compound in the solution.

Cabbage Looper [*Trichoplusia ni* (Hübner)]

Test compounds were diluted in a 50—50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table II under the heading "CL" in terms of percent of the test compound in this solution.

Tobacco Budworm [*Heliothis virescens* (Fabricius)]

Test compounds were diluted in a 50—50 acetone-water solution. Sections of Romaine lettuce (*Latuca sativa*) leaves, approximately 1×1.5 inches, were immersed in the test solutions for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.1% to that at which approximately 50% mortality occurred. LD-50 values are expressed below in Table II under the heading "TBW" in terms of percent of the test compound in the solution.

Southern House Mosquito Larvae [*Culex pipiens quinquefasciatus* (Say)]

Insecticidal activity was determined using third instar larvae of the mosquito *Culex pipiens quinquefasciatus*. Ten larvae were placed in a six ounce paper cup containing 100 milliliters of an aqueous solution of the test chemical. The treated larvae were stored at 70° F., and 48 hours later the mortality was recorded. Test concentrations ranged from 1.0 ppm down to that at which approximately 50% mortality occurred. LD-50 values are expressed below in Table II under the heading "MOS" in terms of ppm of the test compound in the solution.

ACARIDICAL EVALUATION TEST

The two-spotted mite (2SM), *Tetranychus urticae* (Koch), was employed in tests for miticides. The test procedure was as follows:

Pinto bean plants (*Phaseolus* sp.) approximately 10 cm tall, were transplanted into sandy loam soil in 3-inch clay pots and thoroughly infested with two-spotted mites of mixed ages and sexes. 24 hours later the infested plants were inverted and dipped for 2-3 seconds in 50—50 acetone-water solutions of the test chemicals. Treated plants were held in the greenhouse, and 7 days later mortality was determined for both adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs", in terms of percent concentrations of the test compound in the solution.

SYSTEMIC EVALUATION TEST

This test evaluates the root absorption and upward translocation of the candidate systemic compound. The two-spotted mite (2SM) *Tetranychus urticae*, (Koch) and the Bean Aphid (BA)—*Aphis fabae* (Scop.) were employed in the test for systemic activity. Tests were conducted as follows:

Two-Spotted Mite: Test chemicals were dissolved in acetone and aliquots diluted in 200 cc of water in glass bottles. 2 pinto bean plants (*Phaseolus* sp.) with expanded primary leaves, were supported in each bottle by cotton plugs so that their roots and stems were immersed in the treated water. The plugs were then infested with 75-100 two-spotted mites of various ages and sexes. One week later the mortality of the adult mites and nymphs was recorded. Test concentrations of the chemicals in the water ranged from 10 ppm down to that at which 50% mortality occurred.

Black Bean Aphid (Systemic): Test chemicals were diluted in acetone and aliquots thoroughly mixed into 500 grams of dry, sandy loam soil. The treated soil was placed in a pint-sized carton and a nasturtium plant (*Tropaeolum* sp.) approximately 5 cm tall was transplanted into each carton. The plants were then infested with approximately 25 black bean aphids of mixed ages and placed in the greenhouse. 7 days later mortality was recorded. Test concentrations ranged from 10 ppm down to that at which approximately 50% mortality occurred.

LD-50 values are expressed below in Table II under the heading "2SM-SYST", "BA(S)", respectively in terms of percent concentration of the test compound.

TABLE II

| Comp. No. | HF, μg | GR, % | LB, % | BA, % | BA(S) ppm | GPA, % | SMC, % | TBW, % | CL, % | MOS, ppm | 2 - SM PE, % | EGGS % | SYS. ppm |
|---|---|---|---|---|---|---|---|---|---|---|---|---|---|
| 1 | 36 | >0.1 | >0.05 | 0.002 | >10 | 0.03 | >0.05 | >0.1 | >0.1 | 0.1 | <0.05 | <0.05 | >10 |
| 2 | 24 | 0.03 | 0.01 | 0.0003 | >10 | 0.0005 | >0.05 | >0.1 | >0.1 | 0.2 | <0.05 | <0.05 | >10 |
| 3 | 27 | >0.1 | >0.05 | 0.0002 | >10 | 0.0005 | >0.05 | >0.1 | >0.1 | 0.2 | <0.05 | <0.05 | >10 |
| 4 | 75 | >0.1 | >0.05 | 0.002 | >10 | 0.03 | >0.05 | >0.1 | >0.1 | >1 | <0.05 | <0.05 | 8 |
| 5 | 30 | >0.1 | >0.05 | 0.005 | >10 | 0.03 | >0.05 | >0.1 | >0.1 | 0.2 | <0.05 | <0.05 | >10 |
| 6 | 28 | 0.02 | >0.05 | 0.0005 | >10 | >0.05 | >0.05 | >0.1 | 0.1 | 0.03 | <0.05 | <0.05 | >10 |
| 7 | >100 | — | — | 0.005 | >10 | >0.05 | >0.05 | — | — | 0.2 | <0.05 | <0.05 | >10 |
| 8 | 100 | >0.1 | >0.05 | 0.01 | >10 | >0.05 | 0.03 | >0.1 | >0.1 | 0.2 | <0.05 | <0.05 | >10 |
| 9 | >100 | — | — | — | — | >0.05 | >0.05 | — | — | 0.2 | >0.05 | >0.05 | — |
| 10 | 28 | 0.1 | >0.05 | 0.002 | >10 | 0.003 | 0.03 | >0.1 | >0.1 | 0.03 | <0.05 | <0.05 | >10 |
| 11 | 32 | 0.02 | 0.01 | 0.0002 | 10 | 0.001 | >0.05 | 0.1 | >0.1 | 0.03 | <0.05 | <0.05 | 1 |
| 12 | >100 | >0.1 | >0.05 | 0.05 | >10 | >0.05 | >0.05 | >0.1 | >0.1 | 0.03 | <0.05 | <0.05 | >10 |
| 13 | 100 | >0.1 | >0.05 | >0.05 | — | — | 0.03 | >0.1 | >0.1 | 0.3 | <0.05 | <0.05 | >10 |
| 14 | >100 | >0.1 | >0.05 | 0.003 | >10 | 0.03 | >0.05 | 0.1 | >0.1 | 0.08 | <0.05 | <0.05 | >10 |
| 15 | 26 | 0.07 | >0.05 | 0.0002 | >10 | 0.001 | 0.05 | >0.1 | 0.1 | 0.05 | <0.05 | <0.05 | >10 |
| 16 | 59 | >0.1 | >0.05 | >0.05 | — | — | >0.05 | 0.1 | 0.1 | 0.1 | <0.05 | <0.05 | >10 |
| 17 | 35 | 0.1 | >0.05 | 0.0008 | >10 | 0.002 | 0.05 | 0.1 | >0.1 | 0.08 | <0.05 | <0.05 | >10 |
| 18 | 100 | >0.1 | >0.05 | 0.008 | >10 | 0.03 | >0.05 | >0.1 | >0.1 | 0.3 | <0.05 | <0.05 | >10 |
| 19 | 26 | >0.1 | >0.05 | 0.0002 | >10 | 0.03 | >0.05 | >0.1 | >0.1 | 0.05 | <0.05 | <0.05 | >10 |
| 20 | 21 | >0.1 | >0.008 | 0.0003 | >10 | 0.008 | >0.05 | 0.1 | 0.1 | 0.02 | <0.05 | <0.05 | 10 |
| 21 | 52 | >0.1 | >0.05 | — | — | >0.05 | >0.05 | >0.1 | >0.1 | 0.3 | <0.05 | <0.05 | 10 |
| 22 | 27 | 0.06 | 0.006 | 0.0002 | 10 | 0.002 | 0.05 | >0.1 | 0.1 | 0.008 | <0.05 | <0.05 | >10 |
| 23 | 31 | >0.1 | >0.05 | 0.002 | >10 | >0.05 | >0.05 | >0.1 | >0.1 | 0.4 | <0.05 | <0.05 | >10 |
| 24 | 28 | 0.08 | 0.03 | 0.0005 | >10 | 0.001 | 0.05 | 0.1 | >0.1 | 0.02 | <0.05 | <0.05 | >10 |
| 25 | >100 | — | — | — | — | >0.05 | >0.05 | 0.1 | >0.1 | 0.8 | <0.05 | <0.05 | >10 |
| 26 | 36 | 0.09 | 0.03 | 0.0005 | >10 | 0.001 | 0.05 | 0.08 | 0.1 | 0.08 | <0.05 | <0.05 | >10 |
| 27 | 29 | 0.08 | 0.009 | 0.0002 | >10 | 0.001 | 0.05 | 0.01 | 0.1 | 0.008 | <0.05 | <0.05 | >10 |
| 28 | 31 | 0.08 | 0.03 | 0.002 | >10 | >0.05 | 0.03 | 0.02 | 0.01 | 0.008 | <0.05 | <0.05 | >10 |
| 29 | 33 | >0.1 | >0.05 | 0.0008 | — | 0.002 | — | >0.05 | >0.1 | 0.01 | <0.05 | <0.05 | 10 |
| 30 | 30 | >0.1 | 0.05 | 0.005 | — | 0.03 | — | >0.05 | 0.1 | 0.05 | <0.05 | <0.05 | >10 |
| 31 | 32 | >0.1 | >0.05 | 0.002 | — | 0.05 | — | >0.05 | >0.1 | 0.03 | <0.05 | <0.05 | >10 |
| 32 | 30 | 0.08 | >0.05 | 0.001 | — | 0.003 | — | >0.05 | 0.1 | 0.03 | <0.05 | <0.05 | >10 |

TABLE II-continued

| Comp. No. | HF, μg | GR, % | LB, % | BA, % | BA(S) ppm | GPA, % | SMC, % | TBW, % | CL, % | MOS, ppm | 2 - SM PE, % | EGGS % | SYS. ppm |
|---|---|---|---|---|---|---|---|---|---|---|---|---|---|
| 33 | 62 | >0.1 | >0.05 | 0.01 | — | >0.05 | — | >0.05 | >0.1 | 0.1 | 0.05 | <0.05 | >10 |
| 34 | 69 | >0.1 | >0.05 | 0.002 | — | 0.005 | — | >0.05 | >0.1 | 0.2 | <0.05 | <0.05 | >10 |
| 35 | >100 | >0.1 | >0.05 | >0.05 | — | — | — | >0.05 | >0.05 | 1 | 0.05 | >0.05 | — |
| 36 | 33 | >0.1 | >0.05 | 0.002 | — | 0.01 | — | >0.05 | >0.1 | 0.1 | <0.05 | <0.05 | >10 |
| 37 | 69 | >0.1 | >0.05 | 0.003 | — | 0.03 | — | >0.05 | >0.1 | >1 | <0.05 | <0.05 | >10 |
| 38 | 43 | >0.1 | >0.05 | 0.003 | — | 0.03 | — | >0.05 | >0.1 | 0.2 | <0.05 | <0.05 | >10 |
| 39 | >100 | >0.1 | >0.05 | 0.03 | — | >0.05 | — | >0.05 | >0.1 | >1 | >0.05 | >0.05 | — |
| 40 | 100 | >0.1 | >0.05 | 0.002 | — | 0.005 | — | >0.05 | >0.1 | >1 | <0.05 | <0.05 | >10 |
| 41 | 30 | — | — | 0.01 | — | 0.03 | >0.05 | >0.05 | — | — | <0.05 | >0.05 | >10 |

PLANT GROWTH REGULATION EVALUATION

The compounds in Table 1 were tested and found to be active in regulating the growth of plants in various ways. The following tests were performed.

8 Lb./Acre Evaluation

Loamy sand soil pretreated with 100 ppm of 18-18-18 N-P-K fertilizer and 50 ppm of the fungicide cis-N-(trichloromethyl)thio-4-cyclohexene-1,2-dicarboximide, was placed in fiber flats. Seeds of pinto bean (*Phaseolus vulgaris*) were planted in the flats and one two-week old tomato plant was transplanted into each flat. Ten days after seeding the flats were sprayed with solutions containing the test compounds at a rate equivalent to 8 lb./acre (8.96 kg./ha.) active ingredient. The solutions were prepared by weighing out the compounds and dissolving appropriate amounts in acetone containing 1% polyoxyethylene sorbitan monolaurate emulsifying agent. Two weeks after spraying, the plants in the flats were examined for evidence of plant growth regulatory activity.

Table III contains the results for those compounds exhibiting plant growth regulatory activity. All other compounds tested did not exhibit any such activity.

2 Lb./Acre Evaluation

Fiber flats containing loamy sand soil pretreated as above with fertilizer and fungicide were seeded with Cotton ("Acala" variety), Soybeans ("Corsoy" variety), Wheat ("Anza" variety) and Corn ("XL-45" variety). Solutions of selected compounds in Table I were prepared as in the 8 lb. evaluation and were sprayed on the flats 14 days after seeding, at a rate equivalent to 2 lb./acre (2.24 kg./ha.) active ingredient. Two weeks after spraying, the plants in the flats were examined for evidence of plant growth regulatory activity. Results of these tests are contained in Table IV.

The abbreviations in Tables III and IV which follow, indicating the types of growth regulation observed, have the following meaning:
Bl = Bleaching
Cr = Crinkle
E = Epinasty
Eg = Enhanced growth
GR = Growth retarded
LB = Leaf burn
LF = Leaves flaccid
LPL = Large primary leaves
LR = Leaf roll
Mf = Malformations
P = Leaf or bud proliferation
Si = Shortened internodes
Sl = Small leaves
St = Stunting The plant growth regulatory effect was rated on a scale from 0 to 4 with the values indicating the following observations. 0—inactive, no effect; 1—slightly active, 10 to 30% effect; 2—moderately active, 30 to 60%; 3—highly active, 60 to 90%; 4—very highly active, 90 to 100%. Symbols in parenthesis indicate only that slight symptoms of that type were noticed.

TABLE III

| Compound No. | (8 lb./acre) Pinto Bean Rating | Symptom(s) | Tomato Rating | Symptom(s) |
|---|---|---|---|---|
| 30 | 3 | St, Sl, P | 0 | |
| 32 | 3 | P, SI | 0 | |
| 33 | 2 | St, P, Cr | 1 | St |
| 34 | 2 | GR, LPL | 0 | |
| 35 | 2 | SL, Cr, Mf | — | |
| 36 | 3 | EG, SI | 0 | |
| 40 | 2 | Cr, SL, Mf, SI | 0 | |

TABLE IV

| Compound No. | (2 lb./acre) Cotton Rating | Symptom(s) | Soybean Rating | Symptom(s) | Wheat Rating | Corn Rating |
|---|---|---|---|---|---|---|
| 5 | 1 | E | 2 | GR, Cr | 0 | 0 |
| 8 | 0 | | 0 | | 0 | 0 |
| 23 | 3 | GR, Cr | 3 | SI, Cr, SL | 0 | 0 |
| 27 | 3 | Cr, LR | 3 | Cr, SL, Mf, SI | 0 | 0 |
| 30 | 0 | | 0 | | 0 | 0 |
| 32 | 0 | | 0 | | 0 | 0 |
| 33 | 0 | | 2 | GR, Cr, Mf | 0 | 0 |
| 34 | 0 | | — | | — | — |
| 35 | 0 | | — | | — | — |
| 36 | 0 | | — | | — | — |
| 40 | 3 | LF, SI, SL, (Bl) | 2 | Cr, (LB) | 0 | 0 |

In practice, a pure compound can be used as an insecticide. However, in general, the compounds are first formulated with one or more inert (i.e. plant compatible or herbicidally inert) carriers or diluents suitable for insecticidal use, before being applied.

The compositions or formulations, including a compound as described herein, may take and be used in any one of a number of solid or liquid forms. Examples of solid forms are dusts, granules, tablets, powders and the like. Examples of liquid forms are emulsions, solutions, suspensions, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included are wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are also added.

It is possible to use highly concentrated liquid compositions containing up to about 95% by weight of the active compound, or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions and emulsifiable concentrates: 20 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Control of insect pests is accomplished by applying a composition containing an insecticidally effective amount of an active compound as described herein, to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.112 to about 112 kg./ha.).

It should be noted that the active compounds need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus or insect habitat in any conventional manner.

When used in connection with crop or other plant protection, application may be made in a preventive (i.e. before infestation) or eradicative manner (after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

For use as plant growth regulators, the compounds may be included in compositions or formulations in the same manner as for insecticides. Compositions for such use may contain from 0.1 to 95% of the active compound, more preferably from 0.5 to 90%. Some typical plant growth regulatory compositions will contain an active compound as follows: wettable powders —20 to 90% active compound; oil suspensions, emulsions, solutions and emulsifiable concentrates —5 to 90%; aqueous suspensions —10 to 50 %; dusts and powders —1 to 25%; granules and pellets —1 to 20%.

Such compositions may be applied to plants or the locus thereof in the same manner as the insecticides. The rate of application will depend on the acrivity of the compound and the nature and estent of plant growth regulation desired and will vary from about 0.05 to about 50 pounds per acre (about 0.06 to about 56 kg./ha.).

What is claimed is:

1. A method of regulating the growth of plants comprising applying to the plant an effective growth regulating amount of a compound selected from the group consisting of:
- o-ethylmercapto-O,O-diethylphosphorodithioylacetanilide;
- m-ethylmercapto-O,O-diethylphosphorodithioylacetanilide;
- p-ethylmercapto-ethyl-O-isobutylphosphonodithioylacetanilide; and
- p-(n-butylmercapto)-ethyl-O-ethylphosphonodithioylacetanilide.

2. A plant growth regulating composition comprising:

(a) an effective plant growth regulatory amount of a compound selected from the group consisting of:
- o-ethylmercapto-O,O-diethylphosphorodithioylacetanilide;
- m-ethylmercapto-O,O-diethylphosphorodithioylacetanilide;
- p-ethylmercapto-ethyl-O-isobutylphosphonodithioylacetanilide;
- p-(n-butylmercapto)-ethyl-O-ethylphosphonodithioylacetanilide; and (b) an inert carrier or diluent.

* * * * *